United States Patent [19]
Korenberg et al.

[11] Patent Number: 6,166,180
[45] Date of Patent: Dec. 26, 2000

[54] CHROMOSOME 21 GENE MARKER, COMPOSITIONS AND METHODS USING SAME

[75] Inventors: Julie R. Korenberg; Kazuhiro Yamakawa, both of Los Angeles, Calif.

[73] Assignee: Cedar-Sinai Medical Center, Los Angeles, Calif.

[21] Appl. No.: 09/048,887

[22] Filed: Mar. 26, 1998

Related U.S. Application Data

[62] Division of application No. 08/337,690, Nov. 9, 1994, Pat. No. 5,773,268.

[51] Int. Cl.$^7$ .................................................. C07K 14/47
[52] U.S. Cl. .......................................... 530/350; 530/350
[58] Field of Search ............................................ 530/350

[56] References Cited

FOREIGN PATENT DOCUMENTS

WO 93/10228  5/1993  WIPO .

OTHER PUBLICATIONS

Aaltonen et al., 1994, "An autosomal locus causing autoimmune disease: autoimmune polyglandular disease type 1 assigned to chromosome 21", Nature Ge. 8:83–87.

Burmeister et al., 1991, "A map of the distal region of the long arm of human chromosomal 21 constructed by radiation by radiation hybrid mapping and pulsed–field gel electrophoresis", Genomics 9:19–30.

Cheng et al., 1994, Genomics 23:75–84.

Chumakov et al., 1991, "Continuum of overlapping clones spanning the entire human chromosome 21q", Nature 359:380–387.

Cohen et al., 1993 "A first–generation physical map of the human genome", Nature 366:368–701.

Estabrooks et al., 1990, "Holoprosencephaly in an infant with a minute deletion of chromosome 21 (9q22.3)" Am. J. Med. Genet. 36:306–309.

Ghozi et al., 1994, "Isolation, chromosomal localization and sequence analysis of human chromosome 21 zinc finger domain", Genomics 20:487–489.

Griggs et al., 1978, "Hereditary paroxysmal ataxia: response to acetazolamide", Neurology 28:1259–1264.

Hastbacka et al., 1992, "Linkage disequilibrium mapping of DNA sequences unique to human chromosome 21" Nature Genetics 2:204–211.

Jasin et al., 1988, Genes Dev. 2:1353–1363.

Kao et al., 1994, "Isolation and refined regional mapping of expressed sequences for human chromosome 21", Genomics 23:700–703.

Korenberg et al., 1987, "Isolation and regional mapping of DNA sequences unique to human chmosome 21" Am. J.. Hum. Genet. 41:963–979.

Lannfelt et al., 1993, "No linkage to chromosomal 14 in Swedish Alzheimer's disease families", Nature Genetics 4:218–219.

Lehesjoki et al., 1992, "Linkage studies in progressive myoclonus epilepsy: Unverricht–lundborg and lafora's disease", Neurology 42:1545–1550.

Lehesjoki et al., 1993, "Localization of the empl gene or progressive myoclonous epilepsy on chromosome 21: linkage disequilibrium allows high resolution mapping", Hum. Mol. Genet. 2(8): 1229–1234.

Lehesjoki et al., 1994, "PME of Unverricht–Lundborg type in the Mediterranean region: linkage and linkage disequilibium confirm the assignment to the EPM1 locus", Hum. Genet. 93–668–674.

Lehesjoki et al., 1991 "Localization of a gene for progressive myoclonus epilepsy to chromosomal 21q22", PNAS 88:3696–3699.

Madan & Menko, "Intrachromosomal insertions: a case report and review", Human Genet. 89:1–9, 1992.

Malafosse et al., "Identical genetic locus for Baltic and Mediterranean myoclonus", Lancet 339:1080–1081,1992.

McClatchey et al., 1992, "Temperature –sensitive mutations in the III–IV cytoplasmic loop region of skeletal mscle sodium channel gene in paramyotonia congenita" Cell 68:769–779.

Morton, 1991, "Parameters of human genome", PNAS 88:7474–7476.

Mulley et al., 1993, "Refined Genetic localization for central core disease", Am. J. Hum. Genet. 52:398–405.

Munke, 1989, "Clinical cytogenetic and molecular approaches to the genetic heterogeneity of holoprosencephaly" Am. J. Med. Genet. 34:237–245.

Nizetic et al., "Construction, arraying and high–density screening of large insert libraries of human chromosomes X and 21: their potential use as reference libraries", PNAS 88:3233–3237, 1991.

Petersen et al., 1991, "A genetic linkage map of 27 markers on human chromosome 21", Genomics 9: 407–419.

Ptacek et al., 1993, "Genetics and physiology of the myotonic muscle disorders", New Eng. J. Med. 328:482–489.

Ptacek et al., 1991, "Identification of a mutation in the gene causing hyperkalemic periodic paralysis", Cell 77:1021–1027.

Ptacek et al., 1994, "Dihydropyridine receptor mutations cause hypokalamic periodic paralysis" Cell 77:863–868.

Ptacek et al., 1992, "Mutations in an S4 segment of the adult skeletal muscle sodium channel cause paramyotonia congentia", Neuron 8:891–897.

Rojas et al., 1991, "A Met–to–Val mutation in the skeletal muscle Na+ channel α–subunit in hyperkalaemic periodic paralysis", Nature 354–387–369.

(List continued on next page.)

*Primary Examiner*—Robert A. Schwartzman
*Attorney, Agent, or Firm*—Pennie & Edmonds LLP

[57] ABSTRACT

The present invention provides isolated nucleic acids encoding human EHOC-1 protein and isolated receptor proteins encoded thereby. Further provided are vectors containing invention nucleic acids, probes that hybridize thereto, host cells transformed therewith, antisense oligonucleotides thereto and compositions containing, antibodies that specifically bind to invention polypeptides and compositions containing, as well as transgenic non-human mammals that express the invention protein.

6 Claims, 3 Drawing Sheets

OTHER PUBLICATIONS

Shizuya et al., 1992, "Cloning and stable maintenance of 300–kilobase–pair fragments of human DNA in *Escherichia coli* using an F–factor–based vector", PNAS 89:8794–8797.

Tanzi et al., 1992, "A genetic linkage linkage map of human chromosome 21: analysis of recombination as a function of sex and age", Am. J. Hum. Genet. 50–551–558.

Tanzi et al., 1988, "Genetic linkage map of human chromosome 21" Genomics 3:129–136.

Uhlmann et al., 1990, Chemical Rev. 90(4):544–584.

Warren et al., 1989, "A genetic linkage map of 17 markers human chromosome 21" Genomics 4:579–591.

Weissenbach et al., 1992, "A second–generation linkage map of human genome", Nature 359:794–801.

Yamakawa et al., 1995, "Isolation and characterisation of a candidate gene for progressive myoclonus epilepsy and 21q22.3", Human Mol. Genet. 4:(4) 709–716.

Yamakawa et al., 1994, "Holoprosencephaly; characerization of the deletion of 21q22.3 and isolation of cDNAs by direct selection technique" Am. Soc. Hum. Genet. Abstract form.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 5141 base pairs
       (B) TYPE: nucleic acid
       (C) STRANDEDNESS: double
       (D) TOPOLOGY: linear (ii) MOLECULE TYPE: cDNA (vii) IMMEDIATE SOURCE:
       (A) LIBRARY: TRISOMY 21 FETAL BRAIN cDNA LIBRARY
       (B) CLONE: EHOC-1

(viii) POSITION IN GENOME:
       (A) CHROMOSOME/SEGMENT: 21q22.3

(ix) FEATURE:
       (A) NAME/KEY: CDS
       (B) LOCATION: 157..3729

(xi) SEQUENCE DESCRIPTION: SEQ ID NO:1:

```
CTGCAGGAAT CGGCACGAGG CGGCGCAACC GGCTCCGGAG CTGCCTGGCG CGGCCGGGCG        60

GGCGGCGCCG CTCAGGCTCG GGCTCCGGCT GGGCCCGGCG CGGCCTCGGG GCTGCCCATG       120

GGGCGCGGGG GGCCGGGCCG GTGACGCCGG ACGCCC ATG GAC GCC TCT GAG GAG         174
                                        Met Asp Ala Ser Glu Glu
                                         1               5

CCG CTG CCG CCG GTG ATC TAC ACC ATG GAG AAC AAG CCC ATC GTC ACC         222
Pro Leu Pro Pro Val Ile Tyr Thr Met Glu Asn Lys Pro Ile Val Thr
             10                  15                  20

TGT GCT GGA GAT CAG AAT TTA TTT ACC TCT GTT TAT CCA ACG CTC TCT         270
Cys Ala Gly Asp Gln Asn Leu Phe Thr Ser Val Tyr Pro Thr Leu Ser
         25                  30                  35

CAG CAG CTT CCA AGA GAA CCA ATG GAA TGG AGA AGG TCC TAT GGC CGG         318
Gln Gln Leu Pro Arg Glu Pro Met Glu Trp Arg Arg Ser Tyr Gly Arg
     40                  45                  50

GCT CCG AAG ATG ATT CAC CTA GAG TCT AAC TTT GTT CAA TTC AAA GAG         366
Ala Pro Lys Met Ile His Leu Glu Ser Asn Phe Val Gln Phe Lys Glu
 55                  60                  65                  70

GAG CTG CTG CCC AAA GAA GGA AAC AAA GCT CTG CTC ACG TTT CCC TTC         414
Glu Leu Leu Pro Lys Glu Gly Asn Lys Ala Leu Leu Thr Phe Pro Phe
                 75                  80                  85

CTC CAT ATT TAC TGG ACA GAG TGC TGT GAT ACC GAA GTG TAT AAA GCT         462
Leu His Ile Tyr Trp Thr Glu Cys Cys Asp Thr Glu Val Tyr Lys Ala
             90                  95                 100

ACA GTA AAA GAT GAC CTC ACC AAG TGG CAG AAT GTT CTG AAG GCT CAT         510
Thr Val Lys Asp Asp Leu Thr Lys Trp Gln Asn Val Leu Lys Ala His
         105                 110                 115

AGC TCT GTG GAC TGG TTA ATA GTG ATA GTT GAA AAT GAT GCC AAG AAA         558
Ser Ser Val Asp Trp Leu Ile Val Ile Val Glu Asn Asp Ala Lys Lys
     120                 125                 130

AAA AAC AAA ACC AAC ATC CTT CCC CGA ACC TCT ATT GTG GAC AAA ATA         606
Lys Asn Lys Thr Asn Ile Leu Pro Arg Thr Ser Ile Val Asp Lys Ile
135                 140                 145                 150

AGA AAT GAT TTT TGT AAT AAA CAG AGT GAC AGG TGT GTT GTG CTC TCC         654
Arg Asn Asp Phe Cys Asn Lys Gln Ser Asp Arg Cys Val Val Leu Ser
                 155                 160                 165
```

-continued

```
GAC CCC TTG AAG GAC TCT TCT CGA ACT CAG GAA TCC TGG AAT GCC TTC      702
Asp Pro Leu Lys Asp Ser Ser Arg Thr Gln Glu Ser Trp Asn Ala Phe
            170                 175                 180

CTG ACC AAA CTC AGG ACA TTG CTT CTT ATG TCT TTT ACC AAA AAC CTA      750
Leu Thr Lys Leu Arg Thr Leu Leu Leu Met Ser Phe Thr Lys Asn Leu
            185                 190                 195

GGC AAG TTT GAG GAT GAC ATG AGA ACC TTG AGG GAG AAG AGG ACT GAG      798
Gly Lys Phe Glu Asp Asp Met Arg Thr Leu Arg Glu Lys Arg Thr Glu
        200                 205                 210

CCA GGC TGG AGC TTT TGT GAA TAT TTC ATG GTT CAG GAG GAG CTT GCC      846
Pro Gly Trp Ser Phe Cys Glu Tyr Phe Met Val Gln Glu Glu Leu Ala
215                 220                 225                 230

TTT GTT TTC GAG ATG CTG CAG CAG TTC GAG GAC GCC CTG GTG CAG TAC      894
Phe Val Phe Glu Met Leu Gln Gln Phe Glu Asp Ala Leu Val Gln Tyr
                235                 240                 245

GAC GAA CTG GAC GCC CTC TTC TCT CAG TAT GTG GTC AAC TTC GGG GCC      942
Asp Glu Leu Asp Ala Leu Phe Ser Gln Tyr Val Val Asn Phe Gly Ala
            250                 255                 260

GGG GAT GGT GCC AAC TGG CTG ACT TTT TTC TGC CAG CCA GTG AAG AGC      990
Gly Asp Gly Ala Asn Trp Leu Thr Phe Phe Cys Gln Pro Val Lys Ser
            265                 270                 275

TGG AAC GGA TTG ATC CTC CGA AAA CCC ATA GAT ATG GAG AAG CGG GAA     1038
Trp Asn Gly Leu Ile Leu Arg Lys Pro Ile Asp Met Glu Lys Arg Glu
        280                 285                 290

TCG ATC CAG AGG CGA GAA GCC ACC CTG TTA GAT CTG CGC AGT TAC CTG     1086
Ser Ile Gln Arg Arg Glu Ala Thr Leu Leu Asp Leu Arg Ser Tyr Leu
295                 300                 305                 310

TTC TCT CGC CAG TGC ACC TTG CTG CTC TTC CTG CAG AGG CCG TGG GAG     1134
Phe Ser Arg Gln Cys Thr Leu Leu Leu Phe Leu Gln Arg Pro Trp Glu
                315                 320                 325

GTG GCC CAG CGC GCC CTA GAG CTG CTG CAC AAC TGC GTG CAG GAA CTG     1182
Val Ala Gln Arg Ala Leu Glu Leu Leu His Asn Cys Val Gln Glu Leu
            330                 335                 340

AAG CTC TTA GAA GTC TCT GTC CCA CCT GGT GCT CTG GAC TGC TGG GTG     1230
Lys Leu Leu Glu Val Ser Val Pro Pro Gly Ala Leu Asp Cys Trp Val
            345                 350                 355

TTT CTG AGC TGT CTG GAG GTG TTG CAG AGG ATA GAA GGC TGC TGT GAC     1278
Phe Leu Ser Cys Leu Glu Val Leu Gln Arg Ile Glu Gly Cys Cys Asp
        360                 365                 370

CGG GCA CAG ATC GAC TCA AAC ATT GCC CAC ACT GTG GGG CTA TGG AGC     1326
Arg Ala Gln Ile Asp Ser Asn Ile Ala His Thr Val Gly Leu Trp Ser
375                 380                 385                 390

TAT GCC ACA GAA AAG TTA AAG TCC TTG GGC TAT CTA TGT GGA CTT GTG     1374
Tyr Ala Thr Glu Lys Leu Lys Ser Leu Gly Tyr Leu Cys Gly Leu Val
                395                 400                 405

TCA GAG AAA GGA CCT AAC TCA GAA GAT CTC AAC AGG ACA GTT GAC CTT     1422
Ser Glu Lys Gly Pro Asn Ser Glu Asp Leu Asn Arg Thr Val Asp Leu
            410                 415                 420

TTG GCA GGT TTG GGA GCT GAG CGA CCA GAA ACA GCC AAC ACA GCT CAG     1470
Leu Ala Gly Leu Gly Ala Glu Arg Pro Glu Thr Ala Asn Thr Ala Gln
            425                 430                 435

AGT CCT TAT AAG AAA CTG AAA GAA GCA TTA TCG TCA GTG GAA GCT TTT     1518
Ser Pro Tyr Lys Lys Leu Lys Glu Ala Leu Ser Ser Val Glu Ala Phe
        440                 445                 450

GAA AAA CAC TAC TTA GAT TTG TCC CAT GCC ACC ATT GAA ATG TAT ACA     1566
Glu Lys His Tyr Leu Asp Leu Ser His Ala Thr Ile Glu Met Tyr Thr
455                 460                 465                 470

AGC ATT GGG AGG ATT CGA TCT GCT AAG TTT GTT GGA AAA GAT CTG GCA     1614
Ser Ile Gly Arg Ile Arg Ser Ala Lys Phe Val Gly Lys Asp Leu Ala
                475                 480                 485
```

```
GAG TTT TAC ATG AGG AAA AAG GCT CCA CAA AAG GCA GAA ATC TAT CTT       1662
Glu Phe Tyr Met Arg Lys Lys Ala Pro Gln Lys Ala Glu Ile Tyr Leu
            490                 495                 500

CAA GGA GCA CTG AAA AAC TAC CTG GCT GAG GGC TGG GCA CTC CCC ATC       1710
Gln Gly Ala Leu Lys Asn Tyr Leu Ala Glu Gly Trp Ala Leu Pro Ile
            505                 510                 515

ACA CAC ACA AGG AAG CAG CTG GCC GAA TGT CAA AAG CAC CTT GGA CAA       1758
Thr His Thr Arg Lys Gln Leu Ala Glu Cys Gln Lys His Leu Gly Gln
            520                 525                 530

ATT GAA AAC TAC CTG CAG ACC AGC AGC CTC TTA GCC AGT GAC CAC CAC       1806
Ile Glu Asn Tyr Leu Gln Thr Ser Ser Leu Leu Ala Ser Asp His His
535                 540                 545                 550

CTC ACT GAA GAG GAG CGC AAG CAC TTC TGC CAG GAG ATA CTT GAC TTT       1854
Leu Thr Glu Glu Glu Arg Lys His Phe Cys Gln Glu Ile Leu Asp Phe
                555                 560                 565

GCC AGC CAG CCG TCA GAC AGC CCA GGT CAT AAG ATA GTG CTA CCC ATG       1902
Ala Ser Gln Pro Ser Asp Ser Pro Gly His Lys Ile Val Leu Pro Met
            570                 575                 580

CAT TCC TTT GCA CAA CTG CGA GAT CTC CAT TTT GAT CCC TCC AAT GCC       1950
His Ser Phe Ala Gln Leu Arg Asp Leu His Phe Asp Pro Ser Asn Ala
            585                 590                 595

GTG GTC CAC GTG GGC GGC GTT TTG TGC GTT GAG ATA ACC ATG TAC AGC       1998
Val Val His Val Gly Gly Val Leu Cys Val Glu Ile Thr Met Tyr Ser
            600                 605                 610

CAG ATG CCT GTG CCT GTT CAC GTG GAG CAG ATT GTG GTC AAT GTC CAC       2046
Gln Met Pro Val Pro Val His Val Glu Gln Ile Val Val Asn Val His
615                 620                 625                 630

TTC AGC ATT GAG AAA AAC AGC TAC CGG AAG ACT GCG GAG TGG CTT ACC       2094
Phe Ser Ile Glu Lys Asn Ser Tyr Arg Lys Thr Ala Glu Trp Leu Thr
                635                 640                 645

AAG CAC AAG ACG TCC AAT GGG ATC ATT AAC TTT CCA CCC GAG ACC GCA       2142
Lys His Lys Thr Ser Asn Gly Ile Ile Asn Phe Pro Pro Glu Thr Ala
            650                 655                 660

CCT TTC CCT GTA TCC CAA AAC AGT TTG CCC GCG CTG GAG TTG TAT GAA       2190
Pro Phe Pro Val Ser Gln Asn Ser Leu Pro Ala Leu Glu Leu Tyr Glu
            665                 670                 675

ATG TTT GAG AGA AGC CCA TCT GAT AAC TCC TTG AAC ACG ACT GGG ATT       2238
Met Phe Glu Arg Ser Pro Ser Asp Asn Ser Leu Asn Thr Thr Gly Ile
            680                 685                 690

ATC TGC AGA AAC GTC CAC ATG CTC CTG AGA AGG CAG GAG AGC AGC TCC       2286
Ile Cys Arg Asn Val His Met Leu Leu Arg Arg Gln Glu Ser Ser Ser
695                 700                 705                 710

TCT CTA GAG ATG CCC TCA GGG GTG GCT CTG GAG GAG GGT GCC CAC GTG       2334
Ser Leu Glu Met Pro Ser Gly Val Ala Leu Glu Glu Gly Ala His Val
                715                 720                 725

CTG AGG TGC AGC CAC GTG ACC CTG GAA CCA GGG GCC AAC CAG ATA ACA       2382
Leu Arg Cys Ser His Val Thr Leu Glu Pro Gly Ala Asn Gln Ile Thr
            730                 735                 740

TTC AGG ACT CAG GCC AAG GAA CCT GGA ACG TAT ACA CTC AGG CAG CTG       2430
Phe Arg Thr Gln Ala Lys Glu Pro Gly Thr Tyr Thr Leu Arg Gln Leu
            745                 750                 755

TGC GCC TCG GTG GGC TCC GTG TGG TTC GTC CTC CCT CAC ATC TAC CCC       2478
Cys Ala Ser Val Gly Ser Val Trp Phe Val Leu Pro His Ile Tyr Pro
            760                 765                 770

ATT GTG CAG TAC GAC GTG TAC TCA CAG GAG CCC CAG CTG CAC GTG GAG       2526
Ile Val Gln Tyr Asp Val Tyr Ser Gln Glu Pro Gln Leu His Val Glu
775                 780                 785                 790

CCG CTG GCT GAT AGC CTT CTG GCA GGC ATT CCT CAG AGA GTC AAG TTC       2574
Pro Leu Ala Asp Ser Leu Leu Ala Gly Ile Pro Gln Arg Val Lys Phe
```

-continued

```
              795                 800                 805
ACT GTC ACT ACC GGC CAT GAT ACG ATA AAG AAT GGA GAC AGC CTG CAG    2622
Thr Val Thr Thr Gly His Asp Thr Ile Lys Asn Gly Asp Ser Leu Gln
            810                 815                 820

CTT AGC AAT GCC GAA GCC ATG CTC ATC CTG TGC CAG GCG GAG AGC AGG    2670
Leu Ser Asn Ala Glu Ala Met Leu Ile Leu Cys Gln Ala Glu Ser Arg
        825                 830                 835

GCT GTG GTC TAC TCC AAC ACG AGA GAA CAG TCT TCT GAG GCC GCG CTC    2718
Ala Val Val Tyr Ser Asn Thr Arg Glu Gln Ser Ser Glu Ala Ala Leu
    840                 845                 850

CGG ATT CAG TCC TCC GAC AAG GTC ACG AGC ATC AGT CTG CCT GTT GCG    2766
Arg Ile Gln Ser Ser Asp Lys Val Thr Ser Ile Ser Leu Pro Val Ala
855                 860                 865                 870

CCT GCG TAC CAC GTG ATC GAA TTT GAA CTG GAA GTT CTC TCT TTA CCT    2814
Pro Ala Tyr His Val Ile Glu Phe Glu Leu Glu Val Leu Ser Leu Pro
            875                 880                 885

TCA GCC CCA GCA CTC GGA GGG GAG AGT GAC ATG CTG GGG ATG GCA GAG    2862
Ser Ala Pro Ala Leu Gly Gly Glu Ser Asp Met Leu Gly Met Ala Glu
        890                 895                 900

CCC CAC AGG AAG CAT AAG GAC AAA CAG AGA ACT GGC CGC TGC ATG GTT    2910
Pro His Arg Lys His Lys Asp Lys Gln Arg Thr Gly Arg Cys Met Val
    905                 910                 915

ACC ACA GAC CAC AAA GTG TCG ATT GAC TGC CCG TGG TCC ATC TAC TCC    2958
Thr Thr Asp His Lys Val Ser Ile Asp Cys Pro Trp Ser Ile Tyr Ser
920                 925                 930

ACA GTC ATC GCA CTG ACC TTC AGC GTA CCC TTC AGG ACC ACA CAC AGC    3006
Thr Val Ile Ala Leu Thr Phe Ser Val Pro Phe Arg Thr Thr His Ser
            935                 940                 945                 950

CTC CTG TCC TCA GGA ACA CGG AAA TAT GTT CAA GTT TGT GTC CAG AAT    3054
Leu Leu Ser Ser Gly Thr Arg Lys Tyr Val Gln Val Cys Val Gln Asn
        955                 960                 965

TTG TCA GAA CTT GAC TTT CAG CTG TCA GAT AGT TAT CTT GTA GAT ACC    3102
Leu Ser Glu Leu Asp Phe Gln Leu Ser Asp Ser Tyr Leu Val Asp Thr
    970                 975                 980

GGT GAT AGT ACC GAC CTG CAA CTA GTA CCA CTG AAC ACG CAG TCC CAG    3150
Gly Asp Ser Thr Asp Leu Gln Leu Val Pro Leu Asn Thr Gln Ser Gln
985                 990                 995

CAG CCC ATC TAC AGC AAG CAG TCG GTG TTC TTC GTC TGG GAA CTC AAG    3198
Gln Pro Ile Tyr Ser Lys Gln Ser Val Phe Phe Val Trp Glu Leu Lys
            1000                1005                1010

TGG ACA GAA GAG CCT CCC CCT TCT CTG CAT TGC CGG TTC TCT GTT GGA    3246
Trp Thr Glu Glu Pro Pro Pro Ser Leu His Cys Arg Phe Ser Val Gly
1015                1020                1025                1030

TTT TCC CCA GCT TCT GAG GAA CAG CTG TCT ATC TCC TTA AAG CCG TAT    3294
Phe Ser Pro Ala Ser Glu Glu Gln Leu Ser Ile Ser Leu Lys Pro Tyr
        1035                1040                1045

ACT TAT GAA TTT AAA GTG GAA AAT TTT TTT ACA TTA TAC AAC GTG AAG    3342
Thr Tyr Glu Phe Lys Val Glu Asn Phe Phe Thr Leu Tyr Asn Val Lys
    1050                1055                1060

GCT GAG ATC TTT CCC CCT TCG GGA ATG GAG TAT TGC AGA ACA GGC TCC    3390
Ala Glu Ile Phe Pro Pro Ser Gly Met Glu Tyr Cys Arg Thr Gly Ser
            1065                1070                1075

CTC TGC TCC CTG GAG GTT TTG ATC ACG AGG CTC TCA GAC CTC TTG GAG    3438
Leu Cys Ser Leu Glu Val Leu Ile Thr Arg Leu Ser Asp Leu Leu Glu
        1080                1085                1090

GTG GAT AAA GAT GAA GCA CTG ACT GAA TCT GAT GAG CAT TTT TCG ACA    3486
Val Asp Lys Asp Glu Ala Leu Thr Glu Ser Asp Glu His Phe Ser Thr
1095                1100                1105                1110

AAG CTT ATG TAT GAA GTT GTC GAC AAC AGT AGC AAC TGG GCA GTG TGT    3534
```

```
                                    Lys Leu Met Tyr Glu Val Val Asp Asn Ser Ser Asn Trp Ala Val Cys
                                                    1115                1120                1125

GGG AAA AGC TGC GGT GTC ATC TCC ATG CCA GTG GCT GCT CGG GCC ACT          3582
Gly Lys Ser Cys Gly Val Ile Ser Met Pro Val Ala Ala Arg Ala Thr
            1130                1135                1140

CAC AGG GTC CAC ATG GAA GTG ATG CCG CTC TTC GCC GGG TAT CTC CCC          3630
His Arg Val His Met Glu Val Met Pro Leu Phe Ala Gly Tyr Leu Pro
            1145                1150                1155

CTG CCC GAC GTC AGG CTG TTC AAG TAC CTC CCC CAT CAT TCT GCA CAC          3678
Leu Pro Asp Val Arg Leu Phe Lys Tyr Leu Pro His His Ser Ala His
            1160                1165                1170

TCC TCC CAA CTG GAC GCT GAC AGC TGG ATA GAA AAC GCA GCC TGT CAG          3726
Ser Ser Gln Leu Asp Ala Asp Ser Trp Ile Glu Asn Ala Ala Cys Gln
1175                1180                1185                1190

TAGACAAGCA CGGGGACGAC CAGCCGGACA GCAGCAGCCT CAAGAGCAGG GGCAGCGTGC        3786

ATTCGGCCTG CAGCAGCGAG CACAAAGGCC TACCCATGCC CCGGCTGCAG GCACTGCCGG        3846

CCGGCCAGGT CTTCAACTCC AGCTCGGGCA CACAAGTCCT GGTCATCCCC AGCCAAGATG        3906

ACCACGTCCT GGAAGTCAGT GTAACATGAC AACGCCAGGG TGAACACACG CCACTTCCCA       3966

GCTAGGAGTG CACTTTATGG GACTGTGACT GGACTCTTCC GTTCTGGCTC CAGCCAGACC       4026

TTCAGTGGTC CTGCCTGGCC GTGGGGACAT CAGAGAGTGT CATCACGCAG CTGGCCAGCT       4086

GAGTTCTGTT GTTGTTTTCA TGCCGCCTGT GATCTCAGAT TCCTGCTTTT CTCACCCCGT       4146

CCCCATGCTG GTGTCCGACG CCGCTTACTC AGAGCCCTGG CCTCCCTCCC CCTACCTCAC       4206

ACGCTGCTCA TGAAAGTTTC CACCCACGCT GTCTCCACGG AACAGCCTCC GTCTGCTGGC       4266

TCTTCGTGGA AGGCCATTTG TCTTTCAGGT AGACACTCAG CAGCCCTCAC GGTCTTAGTG       4326

ACGTGTGTGC CTTTCTGGTC ACACAGCTGC CCAGTTTCCT GATCGGGGTG GATTTGTGTC       4386

CCCTAAGGGG TAAAACAGCC GTTTACCGCA GATCCTCTCA TACACCCTTC TAGGGGAGGC       4446

GGGTGGGGGA GGGAGGGATC ATAACCCCTT CTGTGCCTTG GGATGCCGGA GCTGGGGGAC       4506

CTGGAGGCCC ATCAGCCGGA GCCACGTGAA AGGTACTGAA GAAAGCTGAG ACCCGGCTGT      4566

GAGGAGCGCC TCAGCGGTGA GGTGGTTTAG GGATAAATGT TTCTGGAACC CTGTGGTCCC       4626

CCATAATGTT GATAGATATC ATATGCACTG GGAGTTAAAT ATATTTAATT TAATGATCAT       4686

TATATATGTG GGGGTTAATA TGTTGTTTTT CTGTCCCTTT AAAGTCTTTA CATGTAATTG      4746

TAGCTGTATA ATCGTTATTT TTCTTTTGCA TCTTAAGTCT TAGAAATTAA GATATTCCAT      4806

CGTGAGGATG AGAGAGGTCC TCAGTGTGTT TTTGGTCTGG TTGTAGGGAA GGACTCAAGT      4866

CCTGGAATGT CCTCCACTGG TCTACTGAGT TGCAGTCACA CTGTTCCAAT GGATTATTTG      4926

CTTTCGGTTG TAAATTTAAT TGTACATATG GTTGATTTAT TATTTTTAAA AATACAGACT      4986

AACTGATGTA ATGTTTATGT ATAAGTTGCA CCAAAAATCA AGGACAAAAA TAAGTGTGTT      5046

TGTTTTTACA GGTGTGAAAG TCACAGCTTG TAAATAAGTG TTGTATGTAT TAAACCTTTT      5106

CCAGTTCTCC AAAAAAAAAA AAAAAAAAAA AAAAA                                  5141

(2) INFORMATION FOR SEQ ID NO:2:

(i) SEQUENCE CHARACTERISTICS:
        (A) LENGTH: 1190 amino acids
        (B) TYPE: amino acid
        (D) TOPOLOGY: linear (ii) MOLECULE TYPE: protein (xi) SEQUENCE DESCRIPTION: SEQ ID NO:2:
```

-continued

```
Met Asp Ala Ser Glu Glu Pro Leu Pro Pro Val Ile Tyr Thr Met Glu
 1               5                  10                  15

Asn Lys Pro Ile Val Thr Cys Ala Gly Asp Gln Asn Leu Phe Thr Ser
             20                  25                  30

Val Tyr Pro Thr Leu Ser Gln Gln Leu Pro Arg Glu Pro Met Glu Trp
             35                  40                  45

Arg Arg Ser Tyr Gly Arg Ala Pro Lys Met Ile His Leu Glu Ser Asn
 50                  55                  60

Phe Val Gln Phe Lys Glu Glu Leu Leu Pro Lys Glu Gly Asn Lys Ala
 65                  70                  75                  80

Leu Leu Thr Phe Pro Phe Leu His Ile Tyr Trp Thr Glu Cys Cys Asp
                 85                  90                  95

Thr Glu Val Tyr Lys Ala Thr Val Lys Asp Asp Leu Thr Lys Trp Gln
                 100                 105                 110

Asn Val Leu Lys Ala His Ser Ser Val Asp Trp Leu Ile Val Ile Val
                 115                 120                 125

Glu Asn Asp Ala Lys Lys Lys Asn Lys Thr Asn Ile Leu Pro Arg Thr
 130                 135                 140

Ser Ile Val Asp Lys Ile Arg Asn Asp Phe Cys Asn Lys Gln Ser Asp
145                 150                 155                 160

Arg Cys Val Val Leu Ser Asp Pro Leu Lys Asp Ser Ser Arg Thr Gln
                 165                 170                 175

Glu Ser Trp Asn Ala Phe Leu Thr Lys Leu Arg Thr Leu Leu Leu Met
                 180                 185                 190

Ser Phe Thr Lys Asn Leu Gly Lys Phe Glu Asp Asp Met Arg Thr Leu
                 195                 200                 205

Arg Glu Lys Arg Thr Glu Pro Gly Trp Ser Phe Cys Glu Tyr Phe Met
 210                 215                 220

Val Gln Glu Glu Leu Ala Phe Val Phe Glu Met Leu Gln Gln Phe Glu
225                 230                 235                 240

Asp Ala Leu Val Gln Tyr Asp Glu Leu Asp Ala Leu Phe Ser Gln Tyr
                 245                 250                 255

Val Val Asn Phe Gly Ala Gly Asp Gly Ala Asn Trp Leu Thr Phe Phe
                 260                 265                 270

Cys Gln Pro Val Lys Ser Trp Asn Gly Leu Ile Leu Arg Lys Pro Ile
                 275                 280                 285

Asp Met Glu Lys Arg Glu Ser Ile Gln Arg Arg Glu Ala Thr Leu Leu
 290                 295                 300

Asp Leu Arg Ser Tyr Leu Phe Ser Arg Gln Cys Thr Leu Leu Leu Phe
305                 310                 315                 320

Leu Gln Arg Pro Trp Glu Val Ala Gln Arg Ala Leu Glu Leu Leu His
                 325                 330                 335

Asn Cys Val Gln Glu Leu Lys Leu Leu Glu Val Ser Val Pro Pro Gly
                 340                 345                 350

Ala Leu Asp Cys Trp Val Phe Leu Ser Cys Leu Glu Val Leu Gln Arg
                 355                 360                 365

Ile Glu Gly Cys Cys Asp Arg Ala Gln Ile Asp Ser Asn Ile Ala His
                 370                 375                 380

Thr Val Gly Leu Trp Ser Tyr Ala Thr Glu Lys Leu Lys Ser Leu Gly
385                 390                 395                 400

Tyr Leu Cys Gly Leu Val Ser Glu Lys Gly Pro Asn Ser Glu Asp Leu
                 405                 410                 415

Asn Arg Thr Val Asp Leu Leu Ala Gly Leu Gly Ala Glu Arg Pro Glu
```

```
                420             425             430
Thr Ala Asn Thr Ala Gln Ser Pro Tyr Lys Lys Leu Lys Glu Ala Leu
            435             440             445
Ser Ser Val Glu Ala Phe Glu Lys His Tyr Leu Asp Leu Ser His Ala
450             455             460
Thr Ile Glu Met Tyr Thr Ser Ile Gly Arg Ile Arg Ser Ala Lys Phe
465             470             475             480
Val Gly Lys Asp Leu Ala Glu Phe Tyr Met Arg Lys Lys Ala Pro Gln
            485             490             495
Lys Ala Glu Ile Tyr Leu Gln Gly Ala Leu Lys Asn Tyr Leu Ala Glu
            500             505             510
Gly Trp Ala Leu Pro Ile Thr His Thr Arg Lys Gln Leu Ala Glu Cys
            515             520             525
Gln Lys His Leu Gly Gln Ile Glu Asn Tyr Leu Gln Thr Ser Ser Leu
            530             535             540
Leu Ala Ser Asp His His Leu Thr Glu Glu Arg Lys His Phe Cys
545             550             555             560
Gln Glu Ile Leu Asp Phe Ala Ser Gln Pro Ser Asp Ser Pro Gly His
            565             570             575
Lys Ile Val Leu Pro Met His Ser Phe Ala Gln Leu Arg Asp Leu His
            580             585             590
Phe Asp Pro Ser Asn Ala Val Val His Val Gly Gly Val Leu Cys Val
            595             600             605
Glu Ile Thr Met Tyr Ser Gln Met Pro Val Pro Val His Val Glu Gln
            610             615             620
Ile Val Val Asn Val His Phe Ser Ile Glu Lys Asn Ser Tyr Arg Lys
625             630             635             640
Thr Ala Glu Trp Leu Thr Lys His Lys Thr Ser Asn Gly Ile Ile Asn
            645             650             655
Phe Pro Pro Glu Thr Ala Pro Phe Pro Val Ser Gln Asn Ser Leu Pro
            660             665             670
Ala Leu Glu Leu Tyr Glu Met Phe Glu Arg Ser Pro Ser Asp Asn Ser
            675             680             685
Leu Asn Thr Thr Gly Ile Ile Cys Arg Asn Val His Met Leu Leu Arg
            690             695             700
Arg Gln Glu Ser Ser Ser Leu Glu Met Pro Ser Gly Val Ala Leu
705             710             715             720
Glu Glu Gly Ala His Val Leu Arg Cys Ser His Val Thr Leu Glu Pro
            725             730             735
Gly Ala Asn Gln Ile Thr Phe Arg Thr Gln Ala Lys Glu Pro Gly Thr
            740             745             750
Tyr Thr Leu Arg Gln Leu Cys Ala Ser Val Gly Ser Val Trp Phe Val
            755             760             765
Leu Pro His Ile Tyr Pro Ile Val Gln Tyr Asp Val Tyr Ser Gln Glu
            770             775             780
Pro Gln Leu His Val Glu Pro Leu Ala Asp Ser Leu Leu Ala Gly Ile
785             790             795             800
Pro Gln Arg Val Lys Phe Thr Val Thr Thr Gly His Asp Thr Ile Lys
            805             810             815
Asn Gly Asp Ser Leu Gln Leu Ser Asn Ala Glu Ala Met Leu Ile Leu
            820             825             830
Cys Gln Ala Glu Ser Arg Ala Val Val Tyr Ser Asn Thr Arg Glu Gln
            835             840             845
```

```
Ser Ser Glu Ala Ala Leu Arg Ile Gln Ser Ser Asp Lys Val Thr Ser
    850                 855                 860

Ile Ser Leu Pro Val Ala Pro Ala Tyr His Val Ile Glu Phe Glu Leu
865                 870                 875                 880

Glu Val Leu Ser Leu Pro Ser Ala Pro Ala Leu Gly Gly Ser Asp
                885                 890                 895

Met Leu Gly Met Ala Glu Pro His Arg Lys His Lys Asp Lys Gln Arg
            900                 905                 910

Thr Gly Arg Cys Met Val Thr Thr Asp His Lys Val Ser Ile Asp Cys
            915                 920                 925

Pro Trp Ser Ile Tyr Ser Thr Val Ile Ala Leu Thr Phe Ser Val Pro
            930                 935                 940

Phe Arg Thr Thr His Ser Leu Leu Ser Ser Gly Thr Arg Lys Tyr Val
945                 950                 955                 960

Gln Val Cys Val Gln Asn Leu Ser Glu Leu Asp Phe Gln Leu Ser Asp
                965                 970                 975

Ser Tyr Leu Val Asp Thr Gly Asp Ser Thr Asp Leu Gln Leu Val Pro
            980                 985                 990

Leu Asn Thr Gln Ser Gln Gln Pro Ile Tyr Ser Lys Gln Ser Val Phe
            995                 1000                1005

Phe Val Trp Glu Leu Lys Trp Thr Glu Glu Pro Pro Ser Leu His
    1010                1015                1020

Cys Arg Phe Ser Val Gly Phe Ser Pro Ala Ser Glu Glu Gln Leu Ser
1025                1030                1035                1040

Ile Ser Leu Lys Pro Tyr Thr Tyr Glu Phe Lys Val Glu Asn Phe Phe
                1045                1050                1055

Thr Leu Tyr Asn Val Lys Ala Glu Ile Phe Pro Pro Ser Gly Met Glu
            1060                1065                1070

Tyr Cys Arg Thr Gly Ser Leu Cys Ser Leu Glu Val Leu Ile Thr Arg
            1075                1080                1085

Leu Ser Asp Leu Leu Glu Val Asp Lys Asp Gly Ala Leu Thr Glu Ser
            1090                1095                1100

Asp Glu His Phe Ser Thr Lys Leu Met Tyr Glu Val Val Asp Asn Ser
1105                1110                1115                1120

Ser Asn Trp Ala Val Cys Gly Lys Ser Cys Gly Val Ile Ser Met Pro
                1125                1130                1135

Val Ala Ala Arg Ala Thr His Val His Met Glu Val Met Pro Leu
            1140                1145                1150

Phe Ala Gly Tyr Leu Pro Leu Pro Asp Val Arg Leu Phe Lys Tyr Leu
            1155                1160                1165

Pro His His Ser Ala His Ser Ser Gln Leu Asp Ala Asp Ser Trp Ile
    1170                1175                1180

Glu Asn Ala Ala Cys Gln
1185                1190

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

-continued (A) ORGANISM: Moraxella bovis
(C) INDIVIDUAL ISOLATE: MboI linker (xi) SEQUENCE DESCRIPTION: SEQ ID NO:3:

CCTGATGCTC GAGTGAATTC                    20

CHROMOSOME 21 GENE MARKER, COMPOSITIONS AND METHODS USING SAME

This application is a divisional of application Ser. No. 08/377,690, filed Nov. 9, 1994 U.S. Pat. No. 5,773,268.

ACKNOWLEDGEMENT

This invention was made in part with Government support under Grant No. HD17449-11, from the National Institutes of Child Health and Human Development. The Government may have certain rights in this invention.

BACKGROUND OF THE INVENTION

A major endeavor in molecular genetics has been made in generating maps of the human genome. Human genome mapping consists, generally, of ordering genomic DNA fragments on their chromosomes using several methods, such as fluorescent in situ hybridization (FISH), somatic cell hybrid analysis or random clone fingerprinting. DNA fragments that correspond to marked polymorphic sites can be ordered by genetic linkage analysis. Distances between polymorphic loci are estimated by meiotic recombination frequencies. High resolution maps based upon the estimated distances, however, cannot be constructed easily using such methods because the resolution is low at the molecular level and recombination frequency is not linearly correlated with physical distance.

Thus, various obstacles such as, for example, the difficulty in obtaining highly informative markers and the paucity of identified markers that are evenly spaced along the chromosome are significant weaknesses of the currently available genetic maps. Most of the mapped markers are restriction fragment length polymorphisms (RFPLs) assayed by DNA hybridization. Although maps based on these markers have contributed greatly to the primary mapping of a number of diseases, they are still insufficient for many applications such as mapping rare monofactorial diseases, refining linkage intervals to distances suited for gene identification, and mapping of loci contributing to complex traits.

Genetic linkage mapping is an important technology applied to the study of human biology and, in particular, for the delineation of the molecular basis of disease. Indeed, one of the most commonly used strategies for studying human inherited diseases is by cloning the responsible gene based on chromosomal location. Genetic linkage maps, therefore, facilitate the identification and mapping of genes involved in monogenic diseases, genes involved in multifactorial disorders, and are useful in carrier detection and prenatal diagnosis of hereditary disorders. A detailed linkage map is also a prerequisite for clone-based physical mapping and DNA sequencing of the entire chromosome.

Human chromosome 21 is a paradigm for large-scale human genome mapping efforts. The smallest human chromosome, chromosome 21 has approximately 50 megabases (Mb) of DNA. Less than 1% of the 2000 genes estimated to be on chromosome 21 are known. A high resolution map of chromosome 21 is of particular interest because of its apparent role in familial Alzheimer disease (FAD), Down's syndrome (DS), amyotrophic lateral sclerosis (ALS), and Finnish progressive myoclonus epilepsy (PME). A gene defect responsible for FAD has been localized to chromosome 21 on the basis of genetic linkage to three pericentromeric loci. The gene encoding the precursor of the Alzheimer-associated amyloid β protein (APP), the principle component of the senile plaques and cerebrovascular amyloid deposits of Alzheimer disease (AD), has also been mapped to chromosome 21.

The process of developing such a long-range contig map involves the identification and localization of landmarks in cloned genetic fragments. When there are enough landmarks for the size of the cloned fragments, contigs are formed, and the landmarks are simultaneously ordered. Currently, YACS, or yeast artificial chromosomes, are utilized for most mapping of the human genome. YACs permit cloning of fragments of a about 500 Kb. However, some difficulties have been encountered with the manipulation of YAC libraries. For example, in various YAC libraries, a fraction of the clones result from co-cloning events, i.e., they include in a single clone noncontiguous DNA fragments. A high percentage of YAC clones, particularly clones having high molecular weight inserts, are chimeric. Chimeric clones map to multiple sites on the chromosome and, thus, hamper the progress of mapping and analysis. Another problem endemic to YAC cloning is caused by DNA segments that are unclonable or unstable and tend to rearrange and delete.

Bacteria Artificial Chromosomes (BACs), provide an alternative to the YAC system. BACs mitigate the most problematic aspects of YACs such as, for example the high rate of chimerism and clonal instability. BACs are based on the $E.\ coli$ single-copy plasmid F factor and are capable of faithful propagation of DNA fragments greater than about 300 Kb in size. BACs have a number of physical properties that make them amenable to physical mapping, including easy manipulation and an absence of chimerism. The lack of chimerism and the capacity to propagate large exogenous insert DNAs make the BACs excellent candidates for chromosome walking and the generation of contiguous physical maps.

The need for molecular description of chromosome 21 derives directly from the association with several human genetic diseases. A map of contiguous units (contigs) covering this chromosome will speed the identification of the cause of these diseases. Indeed, a detailed map would provide immediate access to the genomic segment, including any pathological locus, as soon as it has been localized by genetic linkage or cytogenetic analysis.

Thus, a need exists for identifying, characterizing, and mapping the numerous genes that occupy loci on chromosome 21, which will expedite the rapid translation of high resolution chromosome maps into biological, medical and diagnostic applications. The present invention satisfies this need and provides related advantages as well.

SUMMARY OF THE INVENTION

The present invention provides isolated nucleic acids encoding human EHOC-1 protein and isolated receptor proteins encoded thereby. Further provided are vectors containing invention nucleic acids, probes that hybridize thereto, host cells transformed therewith, antisense oligonucleotides thereto and compositions containing, antibodies that specifically bind to invention polypeptides and compositions containing, as well as transgenic non-human mammals that express the invention protein.

DETAILED DESCRIPTION OF THE INVENTION

Figure 1:
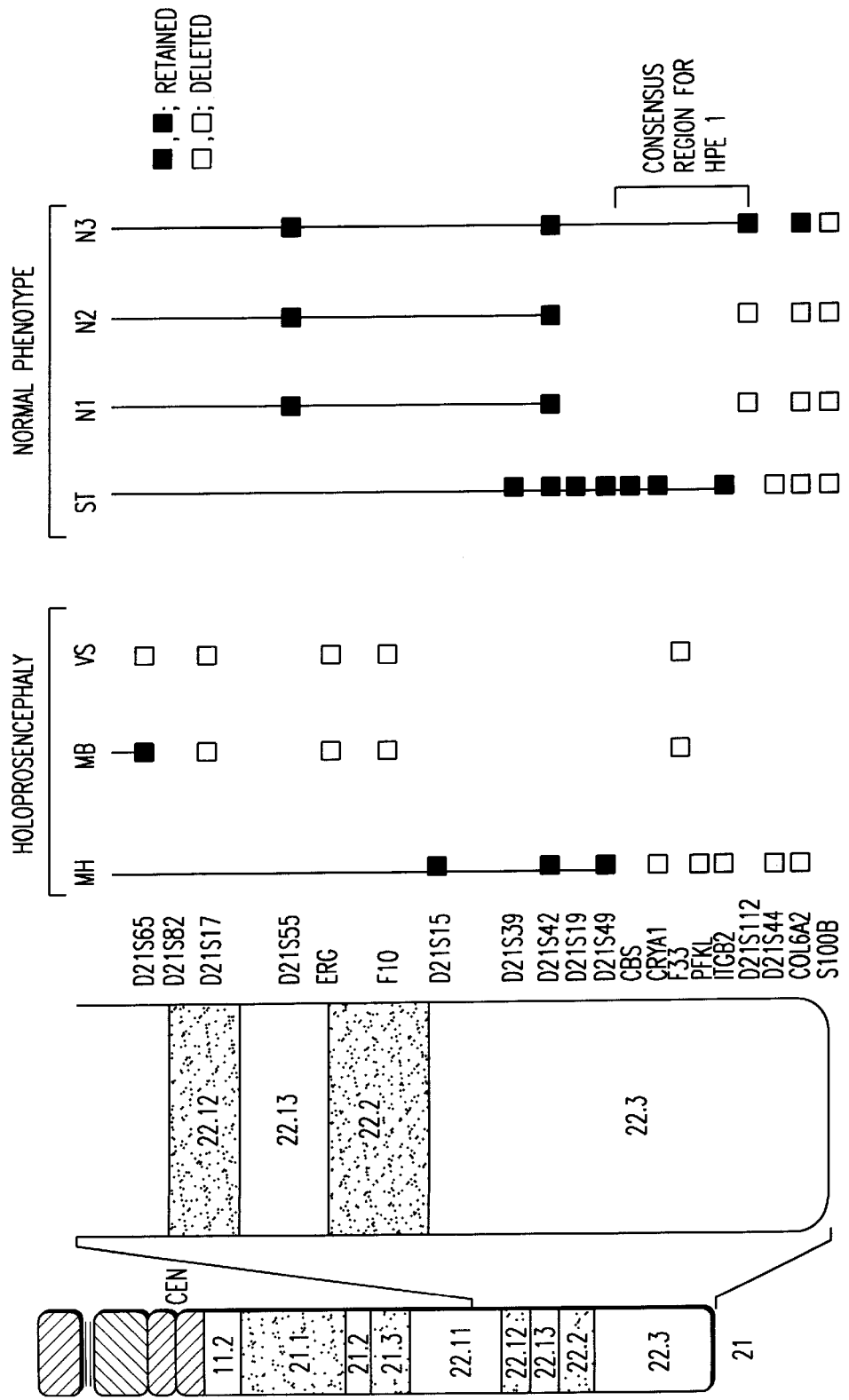
FIG. 1 shows a physical map for the consensus region for HPE1.

Progressive myoclonus epilepsies (PMEs) are a heterogenous group of diseases which are characterized by myoclonus, epileptic seizures and progressive neurological deterioration including ataxia and dementia Berkovic et al., New Engl. J. Med. 315:296–305 (1986). PME of Unverricht-Lundborg type (EPM1) is an autosomal recessive disorder with frequent consanguinity in Finland and Mediterranean regions with the incidence of at least 1:20,000 in Finland. Genetic linkage analysis revealed that the locus for EPM1 is on chromosome 21q22.3 Malafosse et al., Lancet 339:1080–1081 (1992) and excluded Lafora disease from this region which is also a member of PME Lehesjoki et al., Neurology 42:1545–1550 (1992). Linkage disequilibrium analysis made it possible to narrow down the candidate region to 300 kb spanning the loci of PFKL, D21S25 and D21S154 Lehesjoki et al., Hum. Mol. Genet. 2:1229–1234 (1993); Lehesjoki et al., Human Genetics 93:668–674 (1994).

Autoimmune polyglandular disease type I (APECED) was also mapped to chromosome 21q22.3 by linkage disequilibrium analysis Aaltonen, J., et al., Nature Genet. 8:83–87 (1994). APECED is an autosomal recessive disease resulting in a variable combination of failure of the parathyroid glands, adrenal cortex, gonads pancreatic β cells, thyroid gland and gastric parietal cells. Additional affects of APECED include alopecia, vitiligo, hepatitis, chronic mucocutaneous candidiasis, dystrophy of the dental enamel and nails and keratopathy. APCED usually manifests itself in childhood, but tissue specific symptoms may appear throughout adulthood. The APCED locus maps within 500 kb of D21S49 and D21S171.

Holoprosencephaly is characterized by impaired cleavage of the embryonic forebrain and incomplete midfacial development that manifest as a wide range of midfacial anomalies including cyclopia, ethmocephaly cebocephaly, premaxillary agenesis, hypotelorism, and a single maxillary central incisor. The most commonly associated chromosomal abnormality includes dup(3p), del(7 q), deletions of chromosome 13, trisomy 13, trisomy 18, and triploidy (Munke, AM J Med Genet 34:237–245 (1989)). The etiology is heterogeneous and may include aneuploidies for chromosomes 2, 3, 7, 13, 18 and 21. In order to narrow down the candidate region for HPE1, the deletion of 21(q22.3) was characterized in two HP patients by fluorescence in situ hybridization and quantitative Southern blot dosage analysis. For the smaller deletion, the regions for D21S25, D21S154, D21S171 and D21S44 were deleted and for D21S42 and D21S49 were not. Combining these data with previous reports of deletion of 21q22.3 (D21S112-ter) without the holoprosencephaly phenotype indicate that the region responsible for holoprosencephaly spans the 1–2 Mb region including PFKL and ITGB2 (CD18). Four cases of holoprosencephaly with chromosome 21 anomalies have been published. Estabrooks et al. describe a minute deletion of chromosome 21(q22.3) (Estabrooks et al., AM J Med Genet, 36:306–309 (1990)) suggesting this region as a locus for holoprosencephaly (HPE1).

Described in the instant specification is the construction of the BAC (Bacterial Artificial Chromosome) Shizuya et al., Proc. Natl. Acad. Sci. USA 89:8794–8797 (1992) contig of this EPM1-APECED-HPE1 candidate region and the isolation of a novel gene from this contiguous map unit using a direct cDNA selection technique.

In order to isolate genes responsible for these diseases, a cDNA library from a 14-week trisomy 21 fetal brain was constructed using Uni-Zap XR (Stratagene, La Jolla, Calif.). More than 95% clones have inserts ranging from 1–4 kb (avg. 2 kb). In addition, a direct cDNA selection method was applied to BACs (Bacterial Artificial Chromosomes) in the 21q22.3 region. Using cDNA synthesized from trisomy 21 fetal brain, Sau3AI linkers were attached, the cDNA then was digested with Sau3AI, followed by attachment of a second pair of linkers and hybridized to biotinylated BAC DNAs which cover the candidate region. cDNA/BAC DNA hybrid molecules were captured on streptavidin coated magnetic beads, non-specific cDNA were washed out, and specifically hybridized cDNA were eluted and amplified by PCR. Twice selected PCR products were subcloned and analyzed. Southern blot analysis revealed that 21 out of 30 (70%) of fragments yielded unique bands of the original BACs. Using these fragments as probes, cDNAs (3 kb, 4 kb and 5 kb) were isolated from the library. The 5 kb cDNA subclone (EHOC-1) maps proximal to but neighboring D21S25 and showed homologies to transmembrane genes. The loci of these genes all map within the consensus region where holoprosencephaly, EPM1 and APECED are localized.

Figure 3A:
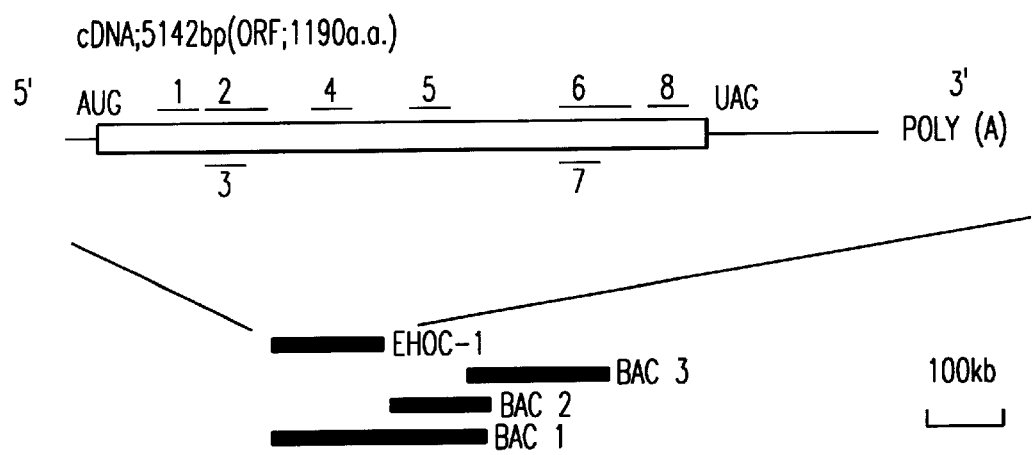
FIG. 3A shows the regions in which EHOC-1 has homologies to transmembrane proteins. Region 1 represents 29.4% identity in a 34 amino acid overlap with rat sodium channel protein III. Region 2 represents 20.4% identity in a 103 amino acid overlap with phosphoglycerate transport system regulatory protein of Salmonella typhimurin. Region 3 represents 29.1% identity in a 55 amino acid overlap with pyrophosphate-energized vacuolar membrane proton pump of Arabidopsis thaliana. Region 4 represents 24.0% identity in a 50 amino acid overlap with myosin-like protein of Saccharomyces cerevisiae. Region 5 represents 17.9% identity in a 39 amino acid overlap with rabbit cardiac muscle ryanodine receptor. Region 6 represents 21.0% identity in a 62 amino acid overlap with rat cardiac muscle sodium channel protein alpha subunit. Region 7 represents 40.7% identity in a 27 amino acid overlap with rat skeletal muscle sodium channel protein alpha subunit. Region 8 represents a 30.3% identity in a 33 amino acid overlap with dystrophin cysteine-rich domain.
Figure 3B:
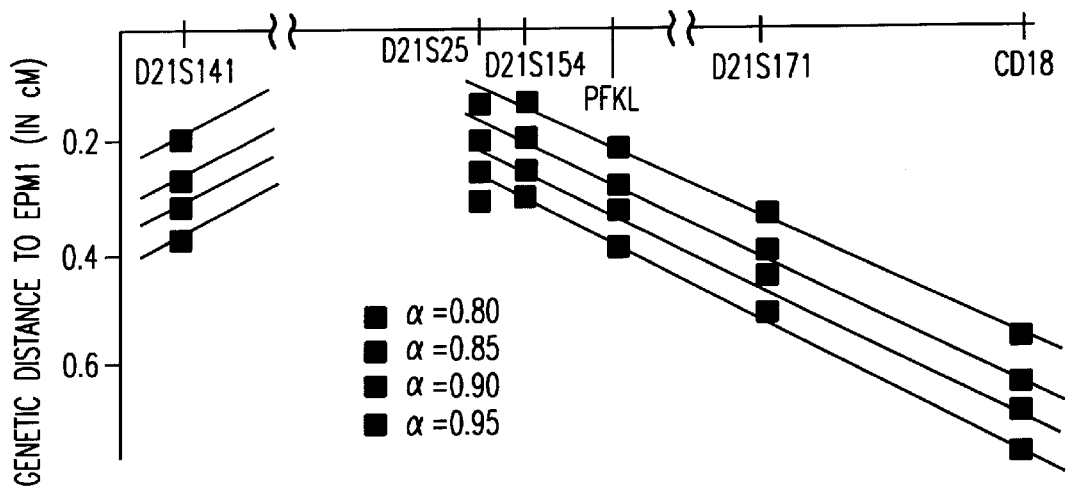
FIG. 3B shows a comparison of genetic distances to the EPM1 locus in centiMorgans as computed by linkage disequilibrium studies. (Lehesjoki et al., Hum. Mol. Genet. 2:1229–1234 (1993)).

DNA sequence analysis of 5 kb cDNA showed a complete coding sequence of 3570 bp which revealed to have homologies to transmembrane proteins including three kinds of sodium channel proteins on amino acid sequence level. (SEQ ID NOS: 1–2; FIG. 3).

Figure 2:
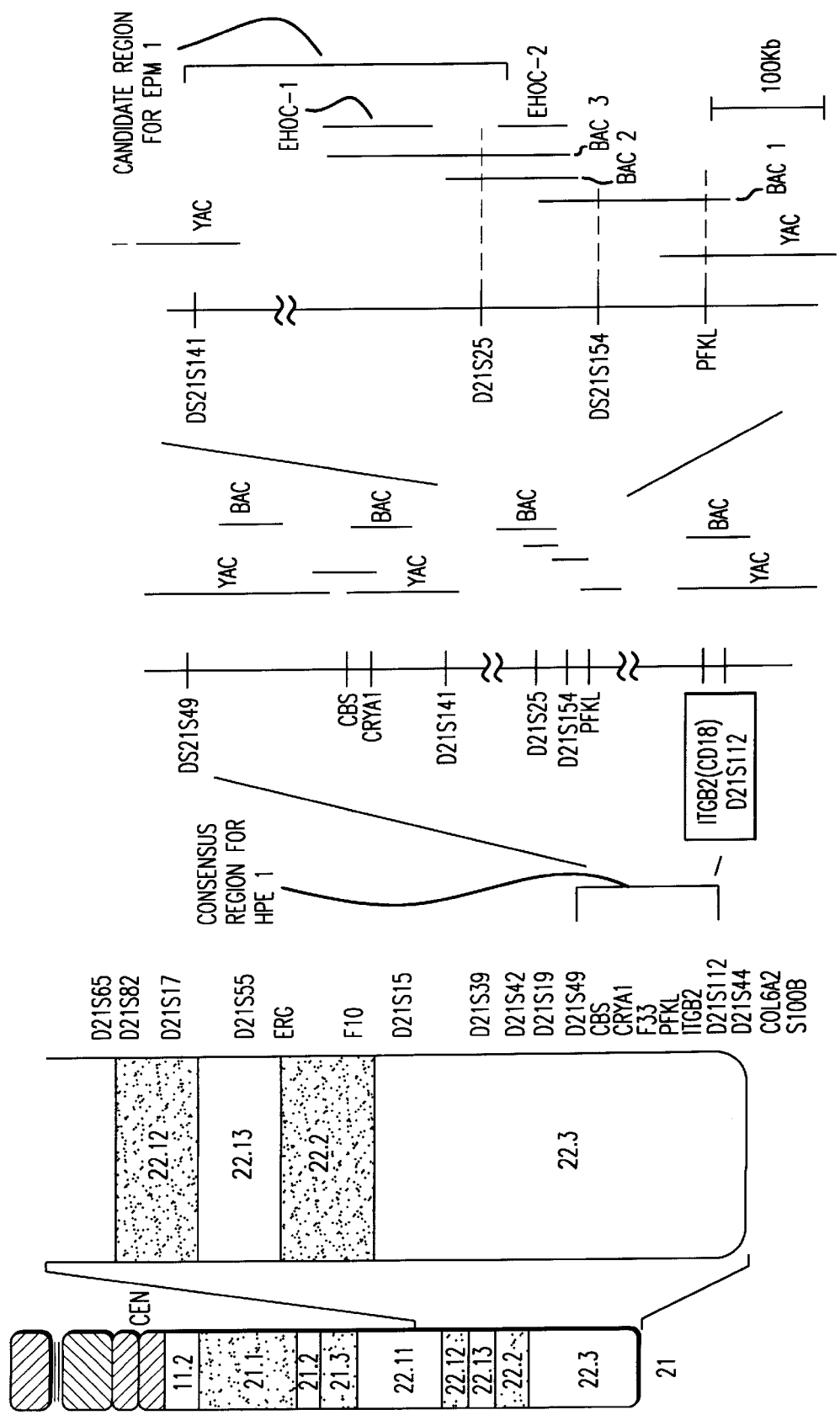
FIG. 2 shows a physical map for the consensus region for EPM1 in relation to the consensus region for HPE1. The locations of YAC clones, BAC clones and EHOC-1 were indicated by thick bars.

Five types of BAC clone were isolated from the total human genomic DNA BAC library Shizuya et al., Proc. Natl. Acad. Sci. USA 89:8794–8797 (1992) by PCR screening method using STSs containing PFKL, D21S25, D21S154 and CD18. Physical maps of the HPE1-EPM1-APECED consensus region with these BAC clones and YAC clones Chumakov et al., Nature 359:380–387 (1992) is described in FIGS. 1 and 2. BAC-1 (230 kb) and BAC-2 (210 kb) were positive for D21S25. BAC-3 (170 kb) was positive for D21S25 and PFKL. Agarose gel electrophoresis of EcoRI-digested BAC DNAs and Southern blot analysis showed that these 3 BACs overlap each other. BAC-4 was identical to BAC-3. BAC-5 (100 kb) was positive for CD18.

Direct cDNA selection was performed on 5 BAC DNAs (four of which were overlapping) which span the consensus region. EcoRI digestion of subclone DNAs revealed that 10% clones were chimeric. The average sizes of the inserts of non-chimeric clones were 400 bp. Forty non-chimeric subclones of selected cDNAs were analyzed by using EcoRI-digested BAC DNA Southern blots. Twenty-eight clones (70%) showed unique signals on the BAC blots, 6 clones (15%) showed repetitive, and 6 clones (15%) did not show any signal on these blots. Using insert DNAs of these subclones as probes, a trisomy 21 fetal brain cDNA library was screened. Three overlapping cDNAs (3 kb, 4 kb and 5 kb) containing poly (A)$^+$ tail were isolated and designated EHOC-1.

The three overlapping EHOC-1 cDNA subclones were used for Southern blot analysis using EcoRI-digested BAC DNA blots. Only BAC-1 showed unique multiple band signals indicating that these cDNAs originated from BAC-1. Identical sizes of the signal bands indicated that these clones overlap each other. Complete sequence of the EHOC-1 5 kb cDNA clone and partial sequence analysis of 3 kb and 4 kb clones showed that entire sequence of the 3 kb clone and part of the sequence of 4 kb clone are contained in the 5 kb clone, but the 3' end of the 4 kb clone was different from that of 5 kb clone indicating the existence of splice variants of EHOC-1 cDNAs. Northern blot analysis using the insert of 5 kb EHOC-1 cDNA revealed three transcripts (5.3 kb, 7.5 kb and Bkb) on multiple adult tissues (heart, brain, placenta, lung, liver, skeletal muscle, kidney, pancreas) Fluorescence in-situ hybridization was also done on lymphocytes of a normal individual using insert of the EHOC-1 5 kb cDNA subclone. Discrete signals were seen on chromosome 21q22.3 confirming the loci. The complete sequence of 5 kb cDNA clone revealed an open reading frame of 3570 bp (1190 amino acid). The initiator ATG was located within a good Kozak consensus sequence Kozak, M., *J. Mol. Biol.* 196:947–950 (1987); Kozak, M., *Nuc. Acid Res.* 15:8125–8148 (1987). Homology search of an amino acid sequence of this ORF to genes registered in Genbank/EMBL showed that this gene product has homologies to multiple transmembrane proteins including three types of sodium channel proteins (FIG. 3).

Some neurologic disorders in humans are known to result from mutations in sodium channels Ptacek et al., Cell 67:1021–1027 (1991); Rojas et al., *Nature* 354:387–389 (1991); McClatchey et al., Cell 68 :769–774 (1992); Ptacek et al., *Neuron* 8:891–897 (1992), calcium channels Ptacek et al., *Cell* 77:863–868 (1994); Jurkut-Rott et al., *Hum. Mol. Genet.* 3:1415–1419 (1994), and a potassium channel Browne et al., *Nature Genet.* 8:136–140 (1994). By using BLAST computer program Altschul, S. J., et al.,*J. Mol. Biol.* 215:403–410 (1994), one fibronectin domain (CxV . . . YxC) was found at 356 <-> 401 a.a. The analysis also showed that the motif (Sxxx(I,L)E) occurs at 462, 670, 708, 716, 730, and 1078. This motif was searched for in various protein databases, and the following are the few where it was present three or more times; rat cartilage specific proteoglycan core protein, myosin, Drosophila sevenless (4 copies), drosophila prospero (4 copies), and Drosophila serendipity (3 copies). The latter three are mutants in development. Sevenless causes an eye defect, prospero defects in axon pathfinding, and serendipity defects in cellularization. It is reasonable that a defect in axonal routing may correlate with the phenotype of EHOC-1. The region beginning at 777 also has some homologies to multiple drug resistance genes and to the drosophila rutabaga gene. Rutabaga is involved in learning in drosophila.

Accordingly, the present invention provides isolated nucleic acids encoding a novel gene, EHOC-1, which exists in human chromosome 21, specifically at the q23.2 locus, which is the site of mutation(s) that cause PME, HPE1, and APECED. The term "nucleic acids" (also referred to as polynucleotides) encompasses RNA as well as single and double-stranded DNA and cDNA. As used herein, the phrase "isolated" means a nucleic acid that is in a form that does not occur in nature. One means of isolating a nucleic acid encoding an EHOC-1 polypeptide is to probe a mammalian genomic library with a natural or artificially designed DNA probe using methods well known in the art. DNA probes derived from the EHOC-1 gene are particularly useful for this purpose. DNA and CDNA molecules that encode EHOC-1 polypeptides can be used to obtain complementary genomic DNA, CDNA or RNA from human, mammalian, or other animal sources, or to isolate related cDNA or genomic clones by the screening of CDNA or genomic libraries, by methods described in more detail below. Examples of nucleic acids are RNA, CDNA, or isolated genomic DNA encoding an EHOC-1 polypeptide. Such nucleic acids may have coding sequences substantially the same as the coding sequence shown in SEQ ID NO: 2. This invention also encompasses nucleic acids which differ from the nucleic acids shown in SEQ ID NO: 1, but which have the same phenotype, i.e., encode substantially the same amino acid sequence set forth in SEQ ID NO: 2.

Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding EHOC-1 polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO: 2. Alternatively, preferred nucleic acids encoding the invention polypeptide(s) hybridize under high stringency conditions to substantially the entire sequence, or substantial portions (i.e., typically at least 15–30 nucleotides) of the nucleic acid sequence set forth in SEQ ID NO: 1.

Stringency of hybridization, as used herein, refers to conditions under which polynucleotide hybrids are stable. As known to those of skill in the art, the stability of hybrids is a function of sodium ion concentration and temperature. (See, for example, Sambrook et al., *Molecular Cloning: A Laboratory Manual* 2d Ed. (Cold Spring Harbor Laboratory, 1989; incorporated herein by reference).

Also provided are isolated peptides, polypeptides(s) and/ or protein(s) encoded by the invention nucleic acids which are EHOC-1 polypeptides. The EHOC-1 polypeptide comprises a protein of approximately 1190 amino acids in length. The predicted amino acid sequence encoding the EHOC-1 polypeptide is set forth in SEQ ID NO: 2.

As used herein, the term "isolated" means a protein molecule free of cellular components and/or contaminants normally associated with a native in vivo environment. Invention polypeptides and/or proteins include any natural occurring allelic variant, as well as recombinant forms thereof. The EHOC-1 polypeptides can be isolated using various methods well known to a person of skill in the art. The methods available for the isolation and purification of invention proteins include, precipitation, gel filtration, ion-exchange, reverse-phase and affinity chromatography. Other well-known methods are described in Deutscher et al., *Guide to Protein Purification: Methods in Enzymology* Vol. 182, (Academic Press, 1990), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the EHOC-1 in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors, described below in more detail. The invention polypeptide, biologically active fragments, and functional equivalents thereof can also be produced by chemical synthesis. As used herein, "biologically active fragment" refers to any portion of the polypeptide represented by the amino acid sequence in SEQ ID NO: 2 that can assemble into a cationic channel permeable to $Ca^{2+}$ which is activated by acetylcholine. Synthetic polypeptides can be produced using Applied Biosystems, Inc. Model 430A or 431A automatic peptide synthesizer (Foster City, Calif.) employing the chemistry provided by the manufacturer.

As used herein, the phrase "EHOC-1"refers to recombinantly expressed/produced (i.e., isolated or substantially pure) proteins that contain highly hydrophobic regions which predict potential membrane spanning regions, having homologies to multiple transmembrane proteins, including sodium channel, calcium channel and potassium channel proteins including variants thereof encoded by mRNA generated by alternative splicing of a primary transcript, and further including fragments thereof which retain one or more of the aforementioned properties. As used herein, the phrase "functional polypeptideII" means that binding of ligands, for example, cause transcriptional activation of EHOC-1 proteins. More specifically, agonist activation of a "functional invention polypeptide" induces the protein to generate a signal.

Modification of the invention nucleic acids, polypeptides or proteins with the following phrases: "recombinantly expressed/produced", "isolated", or "substantially pure", encompasses nucleic acids, peptides, polypeptides or proteins that have been produced in such form by the hand of man, and are thus separated from their native in viva cellular environment. As a result of this human intervention, the recombinant nucleic acids, polypeptides and proteins of the invention are useful in ways that the corresponding naturally occurring molecules are not, such as identification of selective drugs or compounds.

Sequences having "substantial sequence homology" are intended to refer to nucleocide sequences that share at least about 90% identity with invention nucleic acids; and amino acid sequences that typically share at least about 95% amino acid identity with invention polypeptides. It is recognized, however, that polypeptides or nucleic acids containing less than the above-described levels of homology arising as splice variants or that are modified by conservative amino acid substitutions, or by substitution of degenerate codons are also encompassed within the scope of the present invention.

The present invention provides the isolated polynucleotide operatively linked to a promoter of RNA transcription, as well as other regulatory sequences. As used herein, the phrase "operatively linked" refers to the functional relationship of the polynucleotide with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to transacting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, and the like.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. (See, for example, Kozak, *J. Biol. Chem.* 266:19867 (1991)). Similarly, alternative codons, encoding the same amino acid, can be substituted for coding sequences of the EHOC-1 polypeptide in order to enhance transcription (e.g., the codon preference of the host cell can be adopted, the presence of G-C rich domains can be reduced, and the like).

Also provided are vectors comprising the invention nucleic acids. Examples of vectors are viruses, such as baculoviruses and retroviruses, bacteriophages, cosmids, plasmids and other recombination vehicles typically used in the art. Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Also provided are vectors comprising a nucleic acids encoding an EHOC-1 polypeptide, adapted for expression in a bacterial cell, a yeast cell, an amphibian cell (i.e., oocyte), a mammalian cell and other animal cells. The vectors additionally comprise the regulatory elements necessary for expression of the nucleic acid in the bacterial, yeast, amphibian, mammalian or animal cells so located relative to the nucleic acid encoding EHOC-1 polypeptide as to permit expression thereof. As used herein, "expression" refers to the process by which nucleic acids are transcribed into mRNA and translated into peptides, polypeptides, or proteins. If the nucleic acid is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. supra). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention polypeptide.

This invention provides a transformed host cell that recombinantly expresses the EHOC-1 polypeptide. The host cell has been transformed with a nucleic acid encoding a EHOC-1 polypeptide. An example is a mammalian cell comprising a plasmid adapted for expression in a mammalian cell. The plasmid contains a nucleic acid encoding an EHOC-1 polypeptide and the regulatory elements necessary for expression of the invention protein. Various mammalian cells may be utilized as hosts, including, for example, mouse fibroblast cell NIH3T3, CHO cells, HeLa cells, Ltk-cells, etc. Expression plasmids such as those described supra can be used to transfect mammalian cells by methods well known in the art such as calcium phosphate precipitation, DEAE-dextran, electroporation, microinjection or lipofection.

EHOC-1 polypeptides expressed recombinantly on eucaryotic cell surfaces may contain at least one EHOC-1 polypeptide, or may contain a mixture of peptides encoded by the host cell and/or subunits encoded by heterologous nucleic acids.

The present invention provides nucleic acid probes comprising nucleotide sequences capable of specifically hybridizing with sequences included within the nucleic acid sequence encoding an EHOC-1 polypeptide, for example, a coding sequence included within the nucleotide sequence shown in SEQ ID NO: 1. As used herein, a "probe" is a single-stranded DNA or RNA that has a sequence of nucleotides that includes at least 15 contiguous bases set forth in SEQ ID NO: 1. Preferred regions from which to construct probes include 5' and/or 3' coding sequences, sequences within the ORF, sequences predicted to encode transmembrane domains, sequences predicted to encode cytoplasmic loops, signal sequences, ligand binding sites, and the like. Full-length or fragments of cDNA clones can also be used as probes for the detection and isolation of related genes. When fragments are used as probes, preferably the cDNA sequences will be from the carboxyl end-encoding portion of the cDNA, and most preferably will include predicted transmembrane domain-encoding portions of the cDNA sequence. Transmembrane domain regions can be predicted based on hydropathy analysis of the deduced amino acid sequence using, for example, the method of Kyte and Doolittle, *J. Mol. Biol.* 157:105 (1982).

As used herein, the phrase "specifically hybridizing" encompasses the ability of a polynucleotide to recognize a sequence of nucleic acids that are complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding the EHOC-1 polypeptide. For example, the probes can be used for in situ hybridizations in order to locate biological tissues in which the invention gene is expressed. Additionally, synthesized oligonucleotides complementary to the nucleic acids of a nucleotide sequence encoding EHOC-1 polypeptide are useful as probes for detecting the invention genes, their associated MRNA, or for the isolation of related genes using homology screening of genomic or cDNA libraries, or by using amplification techniques well known to one of skill in the art.

Also provided are antisense oligonucleotides having a sequence capable of binding specifically with any portion of an mRNA that encodes the EHOC-1 polypeptide so as to prevent translation of the mRNA. The antisense oligonucleotide may have a sequence capable of binding specifically with any portion of the sequence of the cDNA encoding the EHOC-1 polypeptide. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of the EHOC-1 polypeptide by passing through a cell membrane and binding specifically with mRNA encoding a EHOC-1 polypeptide so as to prevent its translation and an acceptable hydrophobic carrier capable of passing through a cell membrane are also provided herein. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions inhibit translation of mRNA encoding the invention polypeptides. Synthetic oligonucleotides, or other antisense chemical structures are designed to bind to mRNA encoding the EHOC-1 polypeptides and inhibit translation of mRNA and are useful as compositions to inhibit expression of EHOC-1 associated genes in a tissue sample or in a subject.

This invention provides a means to modulate levels of expression of EHOC-1 polypeptides by the use of a synthetic antisense oligonucleotide composition (hereinafter SAOC) which inhibits translation of mRNA encoding these polypeptides. Synthetic oligonucleotides, or other antisense chemical structures designed to recognize and selectively bind to mRNA, are constructed to be complementary to portions of the nucleotide sequences shown in SEQ ID NO: 1 of DNA, RNA or chemically modified, artificial nucleic acids. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations. For example, the SAOC may be designed to bind to a receptor found only in a certain cell type, as discussed supra. The SAOC is also designed to recognize and selectively bind to the target mRNA sequence, which may correspond to a sequence contained within the sequence shown in SEQ ID NO: 1. The SAOC is designed to inactivate the target mRNA sequence by either binding to the target mRNA and inducing degradation of the mRNA by, for example, RNase I digestion, or inhibiting translation of the mRNA target by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS*, 10:435 (1989) and Weintraub, *Sci. American*, January (1990), pp.40; both incorporated herein by reference).

This invention provides a composition containing an acceptable carrier and any of an isolated, purified EHOC-1 polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Also provided are antibodies having specific reactivity with the EHOC-1 polypeptides of the subject invention. Active fragments of antibodies are encompassed within the definition of "antibody".

The antibodies of the invention can be produced by methods known in the art using the invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory 1988), which is incorporated herein by reference. The polypeptide of the present invention can be used as the immunogen in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY 1989) which are incorporated herein by reference).

The invention antibodies can be used to isolate the invention polypeptides. Additionally the antibodies are useful for detecting the presence of the invention polypeptides, as well as analysis of chromosome localization, and structure of functional domains. Methods for detecting the presence of an EHOC-1 polypeptide on the surface of a cell comprise contacting the cell with an antibody that specifically binds to the EHOC-1 polypeptide, under conditions permitting binding of the antibody to the polypeptides, detecting the presence of the antibody bound to the cell, and thereby detecting the presence of the invention polypeptide on the surface of the cell. With respect to the detection of such polypeptides, the antibodies can be used for in vitro diagnostic or in vivo imaging methods.

Immunological procedures useful for in vitro detection of the target EHOC-1 polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Further, invention antibodies can be used to modulate the activity of the EHOC-1 polypeptide in living animals, in humans, or in biological tissues or fluids isolated therefrom. Accordingly, compositions comprising a carrier and an amount of an antibody having specificity for the EHOC-1 polypeptide effective to block binding of naturally occurring ligands to the EHOC-1 polypeptides. A monoclonal antibody directed to an epitope of an EHOC-1 polypeptide molecule present on the surface of a cell and having an amino acid sequence substantially the same as an amino acid sequence for a cell surface epitope of an EHOC-1 polypeptide shown in SEQ ID NO: 2, can be useful for this purpose.

The invention provides a transgenic non-human mammal that is capable of expressing nucleic acids encoding an EHOC-1 polypeptide. Also provided is a transgenic non-human mammal capable of expressing nucleic acids encoding an EHOC-1 polypeptide so mutated as to be incapable of normal activity, i.e., does not express native EHOC-1. The present invention also provides a transgenic non-human mammal having a genome comprising antisense nucleic acids complementary to nucleic acids encoding an EHOC-1 polypeptide so placed as to be transcribed into antisense mRNA complementary to mRNA encoding an EHOC-1 polypeptide, which hybridizes thereto and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO: 1. An example of a non-human transgenic mammal is a transgenic mouse. Examples of tissue specificity-determining elements are the metallothionein promoter and the L7 promoter.

Animal model systems which elucidate the physiological and behavioral roles of EHOC-1 polypeptides are produced by creating transgenic animals in which the expression of the EHOC-1 polypeptide is altered using a variety of techniques. Examples of such techniques include the insertion of normal or mutant versions of nucleic acids encoding an EHOC-1 polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, 1986). Another technique, homologous recombination of mutant or normal versions of these genes with the native gene locus in transgenic animals, may be used to alter the regulation of expression or the structure of the EHOC-1 polypeptide (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of the EHOC-1 polypeptide. In contrast to homologous recombination, microinjection adds genes to the host genome, without removing host genes. Microinjection can produce a transgenic animal that is capable of expressing both endogenous and exogenous EHOC-1 protein. Inducible promoters can be linked to the coding region of the nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

The nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to the invention polypeptide. These in vitro screening assays provide information regarding the function and activity of the invention polypeptide, which can lead to the identification and design of compounds that are capable of specific interaction with one or more types of polypeptides, peptides or proteins.

In accordance with still another embodiment of the present invention, there is provided a method for identifying compounds which bind to EHOC-1 polypeptides. The invention proteins may be employed in a competitive binding assay. Such an assay can accommodate the rapid screening of a large number of compounds to determine which compounds, if any, are capable of binding to EHOC-1 proteins. Subsequently, more detailed assays can be carried out with those compounds found to bind, to further determine whether such compounds act as modulators, agonists or antagonists of invention proteins.

In another embodiment of the invention, there is provided a bioassay for identifying compounds which modulate the activity of invention polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for EHOC-1 polypeptides.

In accordance with another embodiment of the present invention, transformed host cells that recombinantly express invention polypeptides can be contacted with a test compound, and the modulating effect(s) thereof can then be evaluated by comparing the EHOC-1-mediated response (via reporter gene expression) in the presence and absence of test compound, or by comparing the response of test cells or control cells (i.e., cells that do not express EHOC-1 polypeptides), to the presence of the compound.

As used herein, a compound or a signal that "modulates the activity" of an invention polypeptide refers to a compound or a signal that alters the activity of EHOC-1 polypeptides so that the activity of the invention polypeptide is different in the presence of the compound or signal than in the absence of the compound or signal. In particular, such compounds or signals include agonists and antagonists. An agonist encompasses a compound or a signal that activates EHOC-1 protein expression. Alternatively, an antagonist includes a compound or signal that interferes with EHOC-1 protein expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate EHOC-1 activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of EHOC-1 polypeptides can be modulated by contacting the polypeptides with an effective amount of at least one compound identified by the above-described bioassays.

The invention will now be described in greater detail with reference to the following non-limiting examples.

EXAMPLE 1

Construction of BAC Contig

BAC library construction of total human genomic DNA was described elsewhere Shizuya et al., *Proc. Natl. Acad.*

Sci. USA 89:8794–8797 (1992). BAC clones were screened by PCR using STSs (PFKL, D21S25, D21S154, CD18). The loci of these BAC clones were confirmed by fluorescence in-situ hybridization. The sizes of inserts of these clones were measured by running pulsed-field gel electrophoresis after digesting DNA with NotI.

EXAMPLE 2

Direct cDNA Selection

Direct selection procedures were similar to those of Morgan et al. Morgan et al., *Nucleic Acid Res.* 20:5173–5179 (1992) with some modifications. Total RNA was isolated from 14 week trisomy 21 fetal brain using TRI region™ (Molecular Research Center, Inc.). Poly (A)$^+$ RNA was isolated using Poly (A) Quick® mRNA isolation kit (STPATAGENE). Double stranded cDNA was synthesized using SuperScript™ Choice System (GIBCO BRL) from 5 µg trisomy 21 fetal brain poly (A)$^+$ RNA using 1 µg oligo (dT)$_{15}$ or 0.1 µg random hexamer. The entire synthesis reaction was purified by Gene Clean®II kit (BIO101, Inc.) and was kinased. Sau3AI linker was attached to cDNA and digested with Sau3AI. The reaction was purified using Gene Clean. MboI linker I Morgan et al., *Nucleic Acid Res.* 20:5173–5179 (1992) was attached to the cDNA and purified by Gene Clean. Product was amplified by PCR using one strand of MboI linker (5' CCTGATGCTCGAGT-GAATTC3' SEQ ID NO: 3) as a primer. Cycling conditions were 40 cycles of 94° C./15 seconds, 60° C./23 seconds, 72° C./2 minutes in a 100 µl of 1× PCR buffer (Promega), 3 mM $MgCl_2$, 5.0 units of Taq polymerase (Promega), 2 µM primer and 0.2 mM dNTPs. Five kinds of BAC DNA (total 2.5 µg) was prepared using QIAGEN plasmid kit and was biotinylated using Nick Translation Kit and biotin-16-dUTP (Boehringer Manneheim). 3 µg of heat denatured PCR amplified cDNA was annealed with 3 µg of heat denatured COT1 DNA (BRL) in 100 µl hybridization buffer (750 mM NaCl, 50 mM $NaPO_4$ (pH7.2), 5 mM EDTA, 5× Denhardt's, 0.05% SDS and 50% formamide) at 42° C. for two hours. After prehybridization, heat denatured 1.2 µg biotinylated BAC DNA was added and incubated at 42° C. for 16 hours. cDNA-BAC DNA hybrid was precipitated with EtOH and dissolved to 60 µl of 10 mM Tris-HCl (pH 8.0), 1 mM EDTA. After addition of 40 µl 5 M NaCl, the DNA was captured on magnetic beads (Dynabeads M-280, Dynal) at 25° C. for 1 hour with gentle rotating. The beads were washed twice by pipetting in 400 µl of 2× SSC, setting in magnet holder (MPC-E$_{TM}$, Dynal) for 30 seconds and removing supernatant. Four times additional washes were done in 0.2× SSC at 68° C. for 10 minutes each with transferring beads to new tubes at each time. cDNAs were eluted in 100 µl of distilled water for 10 minutes at 80° C. with occasional mixing. The eluted cDNAs were amplified by PCR as described above. After repeating selection procedure on magnetic beads twice, amplified cDNAs were digested with EcoRI and subcloned into pBluescript II.

EXAMPLE 3

Southern Blot Analysis

Gel electrophoresis of DNA was carried out on 0.8% agarose gels in 1× TBE. Transfer of nucleic acids to Nybond N+ nylon membrane (Amersham) was performed by following manufacturer's instruction. Probes were labelled by RadPrime Labeling System (BRL). Hybridization was carried out at 42° C. for 16 hours in 50% formamide, 5× SSPE, 5× Denhardt's 0.1% SDS, 100 µg/ml denatured salmon sperm DNA. The filters were washed once in 1× SSC, 0.1% SDS at room temperature for 20 minutes, twice in 0.1× SSC, 0.1% SDS for 20 minutes a: 65° C. Blots were exposed to X-ray films (Kodak, X-OMAT-AR).

EXAMPLE 4 cDNA Library Screening

A trisomy 21 fetal brain cDNA library was constructed using ZAP-cDNA® synthesis kit (STRATAGENE) which generates unidirectional cDNA library. Briefly, double-stranded cDNA was synthesized from 5 µg trisomy 21 fetal brain poly(A)$^+$ P-NA using a hybrid oligo(dT)-XhoI linker primer with 5-methyl dCTP, attached EcoRI linker, digested with EcoRI and XhoI, and cloned into UNI-ZAP XR vector. The library was packaged using Gigapack® II Gold packaging extract. The titer of the original library was $1.1 \times 10^6$ p.f.u./package. The library was amplified once. Blue-white color assay indicated that 99% clones have inserts. The average size of the inserts was 1.9 kb calculated from 14 clones.

The screening of trisomy 21 fetal brain cDNA library was performed using selected cDNA fragments. Phages were plated to an average density of $1 \times 10^5$ per 175 $cm^2$ plate. Plaque lifts of 20 plates ($2 \times 10^6$ phages) were made using duplicated nylon membranes (Hybond–N+; Amersham). Hybridized membranes were washed to final stringency of 0.2× SSC, 0.1× SDS at 65° C. The filters were exposed to X-ray film overnight. Phages were subcloned into the plasmid vector pBluescript II SK(–) by M13-mediated excision for further analysis.

EXAMPLE 5

Northern Blot Analysis cDNA inserts were cut out from the vector by digestion with XhoI and EcoRI. After labeling using the random priming method, the fragments were used as probes for Northern hybridization using Multiple Tissue Northern Blot (Clontech).

EXAMPLE 6

Metachase Preparation

Chromosomes were prepared by using a BrdU block, (Zabel et al. in *Proc. Natl. Acad. Sci. USA* 80:6932–6936 (1983)) with some modification. Briefly, human peripheral lymphocytes were grown for 72 hours at 37° C. in RPMI 1640 (GISCO BRL, Gaithersburg, Md.) supplemented with L-glutamine (2 mM), 15% fetal calf serum, penicillin (100 IU/ml), streptomycin (0.05 mg/ml) and 0.02% phytohemagglutinin. The cells were blocked in S-phase by adding 5-bromo-deoxyuridine (0.8 mg/ml) for 16 hours. They were then washed once with HBSS (Hanks Balanced Salt Solution) (GIBCO BRL, Gaithersburg, Md.) to remove the synchronizing agent and were released by incubating for five to six more hours in medium supplemented with 2.5 µg/ml of thymidine. Cultures were harvested by the addition of 0.1 µg/ml of colcemid for 10 minutes followed by 0.075 M KCl hypotonic solution for 15 minutes at 37° C. prior to fixation with a 3:1 mixture of methanol and acetic acid, for 1–5 minutes.

What is claimed is:

1. An isolated EHOC-1 polypeptide, wherein said polypeptide has the amino acid sequence set forth in SEQ ID NO: 2.

2. The isolated EHOC-1 polypeptide of claim 1, wherein said polypeptide is encoded by a nucleic acid comprising the nucleotide sequence set forth in SEQ ID NO: 1.

3. An EHOC-1 polypeptide expressed recombinantly in a cell, wherein said polypeptide has the amino acid sequence set forth in SEQ ID NO: 2.

4. The EHOC-1 polypeptide of claim 3, wherein said polypeptide is encoded by a nucleic acid comprising the nucleotide sequence set forth in SEQ ID NO: 1.

5. An isolated EHOC-1 polypeptide, wherein said polypeptide is encoded by a first nucleic acid that hybridizes to a second nucleic acid comprising the nucleotide sequence of SEQ ID NO: 1 under high stringency conditions.

6. A polypeptide having an amino acid sequence corresponding to the sequence of SEQ ID NO: 2 in which at least one amino acid residue has been conservatively substituted.

* * * * *